US 9,005,106 B2

(12) United States Patent
Gross et al.

(10) Patent No.: US 9,005,106 B2
(45) Date of Patent: Apr. 14, 2015

(54) INTRA-AORTIC ELECTRICAL COUNTERPULSATION

(75) Inventors: Yossi Gross, Moshav Mazor (IL); Amir Dagan, Kibbutz Megiddo (IL)

(73) Assignee: Enopace Biomedical Ltd, Caesarean (IL)

( * ) Notice: Subject to any disclaimer, the term of this patent is extended or adjusted under 35 U.S.C. 154(b) by 933 days.

(21) Appl. No.: 12/023,896

(22) Filed: Jan. 31, 2008

(65) Prior Publication Data

US 2009/0198308 A1 Aug. 6, 2009

(51) Int. Cl.
*A61N 1/362* (2006.01)
*A61N 1/36* (2006.01)
*A61N 1/05* (2006.01)
*A61N 1/365* (2006.01)
*A61N 1/39* (2006.01)

(52) U.S. Cl.
CPC .............. *A61N 1/36114* (2013.01); *A61N 1/05* (2013.01); *A61N 1/36564* (2013.01); *A61N 1/3962* (2013.01)

(58) Field of Classification Search
CPC ........... A61B 5/0408; A61B 5/04; A61B 5/02
USPC .............. 607/72; 600/18, 372, 373, 374, 508, 600/481
See application file for complete search history.

(56) References Cited

U.S. PATENT DOCUMENTS

| | | | |
|---|---|---|---|
| 3,650,277 A | 3/1972 | Sjostrand | |
| 3,661,148 A | 5/1972 | Kolin | |
| 4,154,227 A | 5/1979 | Krause et al. | |
| 4,474,630 A | 10/1984 | Planck et al. | |
| 4,692,148 A * | 9/1987 | Kantrowitz et al. | 600/509 |
| 4,791,931 A | 12/1988 | Slate | |
| 4,809,681 A * | 3/1989 | Kantrowitz et al. | 600/17 |
| 4,821,723 A | 4/1989 | Baker, Jr. et al. | |
| 5,192,271 A | 3/1993 | Kalb et al. | |
| 5,265,011 A | 11/1993 | O'Rourke et al. | |
| 5,265,601 A | 11/1993 | Mehra | |
| 5,324,323 A | 6/1994 | Bui | |
| 5,330,507 A | 7/1994 | Schwartz | |
| 5,372,573 A | 12/1994 | Habib | |
| 5,411,031 A | 5/1995 | Yomtov | |

(Continued)

FOREIGN PATENT DOCUMENTS

EP 0109935 5/1984
WO WO9926530 A1 6/1999

(Continued)

OTHER PUBLICATIONS

An International Preliminary Examination Report on Patentability dated Aug. 12, 2010, which issued during the prosecution of Applicant's PCT/IL09/00117.

(Continued)

*Primary Examiner* — Christopher D Koharski
*Assistant Examiner* — Roland Dinga
(74) *Attorney, Agent, or Firm* — Fish & Richardson P.C.

(57) ABSTRACT

In some embodiments of the present invention, apparatus is provided, including a sensing electrode configured to be implanted at a non-cardiac site in a vicinity of an aorta of a subject and to detect an electrical parameter of the aorta, and a control unit configured to receive the detected parameter and to generate an output in response to the detected parameter. Additional embodiments are also described.

13 Claims, 11 Drawing Sheets

(56) References Cited

U.S. PATENT DOCUMENTS

| | | | |
|---|---|---|---|
| 5,423,871 | A | 6/1995 | Hoegnelid et al. |
| 5,458,626 | A | 10/1995 | Krause |
| 5,487,760 | A | 1/1996 | Villafana |
| 5,540,730 | A | 7/1996 | Terry |
| 5,571,150 | A | 11/1996 | Wernicke |
| 5,612,314 | A | 3/1997 | Stamler et al. |
| 5,645,839 | A | 7/1997 | Chobanian et al. |
| 5,649,966 | A | 7/1997 | Noren et al. |
| 5,651,378 | A | 7/1997 | Matheny |
| 5,669,924 | A | 9/1997 | Shaknovich |
| 5,690,681 | A | 11/1997 | Geddes |
| 5,707,400 | A | 1/1998 | Terry |
| 5,735,887 | A | 4/1998 | Barreras |
| 5,762,599 | A | 6/1998 | Sohn |
| 5,782,774 | A | 7/1998 | Shmulewitz |
| 5,800,464 | A | 9/1998 | Kieval |
| 5,800,502 | A | 9/1998 | Boutos |
| 5,900,433 | A | 5/1999 | Igo et al. |
| 5,902,712 | A | 5/1999 | Burns et al. |
| 5,904,711 | A | 5/1999 | Flom |
| 5,904,712 | A | 5/1999 | Axelgaard |
| 5,906,641 | A | 5/1999 | Thompson et al. |
| 5,913,876 | A | 6/1999 | Taylor |
| 5,916,239 | A | 6/1999 | Geddes |
| 5,925,061 | A | 7/1999 | Ogi et al. |
| 5,935,077 | A | 8/1999 | Ogle |
| 5,948,006 | A | 9/1999 | Mann |
| 5,967,986 | A | 10/1999 | Cimochowski et al. |
| 5,994,444 | A | 11/1999 | Trescony et al. |
| 6,023,640 | A | 2/2000 | Ross |
| 6,038,485 | A | 3/2000 | Axelgaard |
| 6,053,873 | A | 4/2000 | Govari et al. |
| 6,058,331 | A | 5/2000 | King |
| 6,086,527 | A | 7/2000 | Talpade |
| 6,104,956 | A | 8/2000 | Naritoku |
| 6,106,477 | A | 8/2000 | Miesel et al. |
| 6,120,520 | A | 9/2000 | Saadat |
| 6,141,587 | A | 10/2000 | Mower |
| 6,200,259 | B1 | 3/2001 | March |
| 6,201,991 | B1 | 3/2001 | Chekanov |
| 6,245,103 | B1 | 6/2001 | Stinson |
| 6,277,078 | B1 | 8/2001 | Porat et al. |
| 6,317,631 | B1 | 11/2001 | Ben-Haim et al. |
| 6,339,725 | B1 | 1/2002 | Naritoku |
| 6,347,247 | B1 | 2/2002 | Dev et al. |
| 6,411,845 | B1 | 6/2002 | Mower |
| 6,445,953 | B1 | 9/2002 | Bulkes et al. |
| 6,463,323 | B1 | 10/2002 | Conrad-Vlasak et al. |
| 6,473,644 | B1 | 10/2002 | Terry |
| 6,485,524 | B2 | 11/2002 | Strecker et al. |
| 6,496,732 | B1 | 12/2002 | Wallace |
| 6,522,926 | B1 | 2/2003 | Kieval |
| 6,532,388 | B1 | 3/2003 | Hill |
| 6,611,715 | B1 | 8/2003 | Boveja |
| 6,615,085 | B1 | 9/2003 | Boveja |
| 6,616,613 | B1 | 9/2003 | Goodman et al. |
| 6,622,041 | B2 | 9/2003 | Terry |
| 6,631,296 | B1 | 10/2003 | Parramon |
| 6,632,991 | B2 | 10/2003 | Chen |
| 6,647,287 | B1 | 11/2003 | Peel et al. |
| 6,656,960 | B2 | 12/2003 | Puskas |
| 6,668,191 | B1 | 12/2003 | Boveja |
| 6,721,603 | B2 | 4/2004 | Zabara et al. |
| 6,810,286 | B2 | 10/2004 | Donovan et al. |
| 6,824,561 | B2 | 11/2004 | Soykan et al. |
| 6,845,267 | B2 | 1/2005 | Harrison et al. |
| 6,865,416 | B2 * | 3/2005 | Dev et al. ............ 607/2 |
| 6,871,092 | B2 | 3/2005 | Piccone et al. |
| 6,885,895 | B1 | 4/2005 | Whitehurst et al. |
| 6,934,583 | B2 | 8/2005 | Weinberg |
| 6,939,345 | B2 | 9/2005 | KenKnight et al. |
| 6,947,792 | B2 | 9/2005 | Ben-Haim et al. |
| 6,957,107 | B2 | 10/2005 | Rogers |
| 7,062,318 | B2 | 6/2006 | Ben-Haim et al. |
| 7,076,307 | B2 | 7/2006 | Boveja |
| 7,079,901 | B1 | 7/2006 | Loftin |
| 7,082,336 | B2 | 7/2006 | Ransbury et al. |
| 7,090,648 | B2 | 8/2006 | Sackner et al. |
| 7,149,574 | B2 | 12/2006 | Yun |
| 7,167,751 | B1 | 1/2007 | Whitehurst et al. |
| 7,191,012 | B2 | 3/2007 | Boveja |
| 7,201,719 | B2 | 4/2007 | Feliss |
| 7,206,637 | B2 | 4/2007 | Salo |
| 7,225,019 | B2 | 5/2007 | Jahns |
| 7,228,167 | B2 | 6/2007 | Kara |
| 7,229,403 | B2 | 6/2007 | Schock et al. |
| 7,263,405 | B2 | 8/2007 | Boveja |
| 7,269,457 | B2 | 9/2007 | Shafer et al. |
| 7,277,761 | B2 | 10/2007 | Shelchuk |
| 7,291,113 | B2 | 11/2007 | Satoh et al. |
| 7,292,886 | B1 | 11/2007 | Kroll |
| 7,299,091 | B2 | 11/2007 | Barrett et al. |
| 7,321,793 | B2 | 1/2008 | Ben Ezra et al. |
| 7,363,076 | B2 | 4/2008 | Yun |
| 7,444,183 | B2 | 10/2008 | Knudson |
| 7,452,334 | B2 | 11/2008 | Gianchandani et al. |
| 7,471,986 | B2 | 12/2008 | Hatlestad |
| 7,476,200 | B2 | 1/2009 | Tal |
| 7,480,532 | B2 | 1/2009 | Kieval |
| 7,486,991 | B2 | 2/2009 | Libbus |
| 7,499,747 | B2 | 3/2009 | Kieval |
| 7,499,748 | B2 | 3/2009 | Moffitt |
| 7,502,650 | B2 | 3/2009 | Kieval |
| 7,519,421 | B2 | 4/2009 | Denker |
| 7,555,344 | B2 | 6/2009 | Maschino |
| 7,561,918 | B2 | 7/2009 | Armstrong |
| 7,570,999 | B2 | 8/2009 | Libbus |
| 7,613,511 | B2 | 11/2009 | Wu |
| 7,613,515 | B2 | 11/2009 | Knudson |
| 7,617,003 | B2 | 11/2009 | Caparso |
| 7,623,926 | B2 | 11/2009 | Rossing |
| 7,634,315 | B2 | 12/2009 | Cholette |
| 7,706,875 | B2 | 4/2010 | Buras |
| 7,706,884 | B2 | 4/2010 | Libbus |
| 7,706,886 | B2 | 4/2010 | Morimoto et al. |
| 7,715,915 | B1 | 5/2010 | Ryu |
| 7,720,547 | B2 | 5/2010 | Denker |
| 7,725,194 | B2 | 5/2010 | Klostermann |
| 7,738,961 | B2 | 6/2010 | Sharma |
| 7,747,302 | B2 | 6/2010 | Milledge et al. |
| 7,765,000 | B2 | 7/2010 | Zhang et al. |
| 7,765,008 | B2 | 7/2010 | Ben-Haim |
| 7,769,446 | B2 | 8/2010 | Moffitt |
| 7,801,604 | B2 | 9/2010 | Brockway |
| 7,811,221 | B2 | 10/2010 | Gross |
| 7,813,805 | B1 | 10/2010 | Farazi |
| 7,813,812 | B2 | 10/2010 | Kieval |
| 7,826,899 | B1 | 11/2010 | Ryu |
| 7,848,820 | B2 | 12/2010 | Abrahamson |
| 7,856,273 | B2 | 12/2010 | Maschino |
| 7,860,566 | B2 | 12/2010 | Mazgalev |
| 7,869,870 | B1 | 1/2011 | Farazi |
| 7,881,782 | B2 | 2/2011 | Libbus |
| 7,881,792 | B1 | 2/2011 | Farazi |
| 7,894,902 | B2 | 2/2011 | Rom |
| 7,949,400 | B2 | 5/2011 | Kieval |
| 7,991,474 | B2 | 8/2011 | Aldrich |
| 8,046,085 | B2 | 10/2011 | Knudson |
| 8,065,019 | B2 | 11/2011 | Marnfeldt |
| 8,086,314 | B1 | 12/2011 | Kieval |
| 8,121,692 | B2 | 2/2012 | Haefner |
| 8,131,362 | B2 | 3/2012 | Moffitt |
| 8,150,508 | B2 | 4/2012 | Craig |
| 8,224,437 | B2 | 7/2012 | Kieval |
| 8,244,378 | B2 | 8/2012 | Bly |
| 8,249,705 | B1 | 8/2012 | Kieval |
| 8,386,038 | B2 | 2/2013 | Bianchi |
| 8,391,970 | B2 | 3/2013 | Tracey |
| 8,406,868 | B2 | 3/2013 | Buschman |
| 8,442,639 | B2 | 5/2013 | Walker |
| 8,449,472 | B2 | 5/2013 | Ryu |
| 8,457,743 | B2 | 6/2013 | Gollasch |
| 8,457,748 | B2 | 6/2013 | Lange |
| 8,463,392 | B2 | 6/2013 | Aghassian |

(56) References Cited

U.S. PATENT DOCUMENTS

| | | |
|---|---|---|
| 8,467,884 B2 | 6/2013 | Chen |
| 8,478,414 B2 | 7/2013 | Kieval |
| 8,498,704 B2 | 7/2013 | Shuros |
| 8,504,161 B1 | 8/2013 | Kornet |
| 8,509,919 B2 | 8/2013 | Yoo |
| 8,521,293 B2 | 8/2013 | Anderson |
| 8,538,535 B2 | 9/2013 | Gross |
| 8,538,542 B2 | 9/2013 | Knudson |
| 8,560,076 B2 | 10/2013 | Kieval |
| 8,571,654 B2 | 10/2013 | Libbus |
| 8,571,664 B2 | 10/2013 | Anderson |
| 8,577,458 B1 | 11/2013 | Libbus |
| 8,600,505 B2 | 12/2013 | Libbus |
| 8,600,511 B2 | 12/2013 | Yared |
| 8,600,521 B2 | 12/2013 | Armstrong |
| 8,606,359 B2 | 12/2013 | Rossing |
| 8,612,014 B2 | 12/2013 | Rahman |
| 8,620,422 B2 | 12/2013 | Kieval |
| 8,620,450 B2 | 12/2013 | Tockman |
| 8,626,290 B2 | 1/2014 | Dagan |
| 8,626,299 B2 | 1/2014 | Gross |
| 8,630,709 B2 | 1/2014 | Libbus |
| 8,634,928 B1 | 1/2014 | O'Driscoll et al. |
| 8,639,327 B2 | 1/2014 | Zhou |
| 8,639,339 B2 | 1/2014 | Bange |
| 8,644,928 B2 | 2/2014 | Takata |
| 8,660,666 B2 | 2/2014 | Craig |
| 8,663,103 B2 | 3/2014 | Causey |
| 8,670,835 B2 | 3/2014 | Park |
| 8,700,145 B2 | 4/2014 | Kilgard |
| 8,700,157 B2 | 4/2014 | Goetz |
| 8,700,173 B2 | 4/2014 | Edlund |
| 8,706,223 B2 | 4/2014 | Zhou |
| 8,712,531 B2 | 4/2014 | Kieval |
| 8,729,129 B2 | 5/2014 | Tracey |
| 8,731,663 B2 | 5/2014 | Bianchi |
| 8,738,126 B2 | 5/2014 | Craig |
| 8,744,586 B2 | 6/2014 | Georgakopoulos |
| 8,755,907 B2 | 6/2014 | Kieval |
| 8,788,028 B2 | 7/2014 | Kumar |
| 8,788,066 B2 | 7/2014 | Cates |
| 8,805,513 B2 | 8/2014 | Libbus |
| 8,818,508 B2 | 8/2014 | Scheiner |
| 8,818,524 B2 | 8/2014 | Hincapie |
| 2001/0044434 A1 | 11/2001 | Lee et al. |
| 2002/0016615 A1 | 2/2002 | Dev |
| 2002/0026228 A1 | 2/2002 | Schauerte |
| 2002/0032468 A1 | 3/2002 | Hill et al. |
| 2002/0077554 A1 | 6/2002 | Schwartz et al. |
| 2002/0103454 A1 | 8/2002 | Sackner et al. |
| 2002/0169413 A1 | 11/2002 | Keren et al. |
| 2003/0036773 A1 | 2/2003 | Whitehurst et al. |
| 2003/0050683 A1 | 3/2003 | Boutos |
| 2003/0055465 A1 | 3/2003 | Ben-Haim et al. |
| 2003/0055466 A1 | 3/2003 | Ben-Haim et al. |
| 2003/0055467 A1 | 3/2003 | Ben-Haim et al. |
| 2003/0060858 A1 | 3/2003 | Kieval et al. |
| 2003/0130715 A1 | 7/2003 | Boutos |
| 2003/0204206 A1 | 10/2003 | Padua et al. |
| 2004/0010303 A1 | 1/2004 | Bolea |
| 2004/0019364 A1 | 1/2004 | Kieval |
| 2004/0039417 A1 | 2/2004 | Soykan et al. |
| 2004/0044393 A1 | 3/2004 | Yarden |
| 2004/0054384 A1 | 3/2004 | Nachum |
| 2004/0064090 A1 | 4/2004 | Keren et al. |
| 2004/0106954 A1* | 6/2004 | Whitehurst et al. ............. 607/3 |
| 2004/0111006 A1* | 6/2004 | Alferness et al. .............. 600/16 |
| 2004/0133240 A1 | 7/2004 | Adams et al. |
| 2004/0162590 A1 | 8/2004 | Whitehurst et al. |
| 2005/0049680 A1 | 3/2005 | Fischell et al. |
| 2005/0090867 A1 | 4/2005 | Lapanashvili |
| 2005/0143785 A1 | 6/2005 | Libbus |
| 2005/0149130 A1 | 7/2005 | Libbus |
| 2005/0149132 A1 | 7/2005 | Libbus |
| 2005/0149155 A1 | 7/2005 | Scheiner et al. |
| 2005/0154418 A1 | 7/2005 | Kieval et al. |
| 2005/0209652 A1 | 9/2005 | Whitehurst et al. |
| 2005/0233962 A1 | 10/2005 | Lue et al. |
| 2005/0240229 A1 | 10/2005 | Whitehurst et al. |
| 2005/0288651 A1 | 12/2005 | VanTassel |
| 2006/0100668 A1 | 5/2006 | Ben-David et al. |
| 2006/0149124 A1 | 7/2006 | Forsell |
| 2006/0149345 A1 | 7/2006 | Boggs et al. |
| 2006/0167540 A1* | 7/2006 | Masters et al. ............... 623/1.44 |
| 2006/0173507 A1 | 8/2006 | Mrva et al. |
| 2006/0217588 A1* | 9/2006 | Gross et al. ...................... 600/16 |
| 2006/0217772 A1 | 9/2006 | Libbus et al. |
| 2006/0229677 A1 | 10/2006 | Moffit et al. |
| 2006/0259085 A1 | 11/2006 | Zhang et al. |
| 2006/0276844 A1 | 12/2006 | Alon et al. |
| 2007/0021673 A1 | 1/2007 | Arbel et al. |
| 2007/0021786 A1 | 1/2007 | Parnis et al. |
| 2007/0021792 A1 | 1/2007 | Kieval et al. |
| 2007/0027496 A1 | 2/2007 | Parnis et al. |
| 2007/0100433 A1 | 5/2007 | Limon |
| 2007/0142879 A1 | 6/2007 | Greenberg et al. |
| 2007/0150009 A1* | 6/2007 | Kveen et al. ...................... 607/9 |
| 2007/0156179 A1 | 7/2007 | S.E. |
| 2007/0185540 A1 | 8/2007 | Ben-Haim |
| 2007/0185542 A1 | 8/2007 | Bolea et al. |
| 2007/0185543 A1 | 8/2007 | Rossing et al. |
| 2007/0191904 A1 | 8/2007 | Libbus |
| 2007/0196428 A1 | 8/2007 | Glauser et al. |
| 2007/0198064 A1 | 8/2007 | Lapanashvili et al. |
| 2007/0248676 A1 | 10/2007 | Stamler et al. |
| 2007/0248850 A1* | 10/2007 | Heller ............................. 429/13 |
| 2007/0276270 A1* | 11/2007 | Tran ............................. 600/508 |
| 2007/0293927 A1* | 12/2007 | Frank et al. .................. 623/1.11 |
| 2008/0021336 A1 | 1/2008 | Dobak |
| 2008/0051849 A1 | 2/2008 | Ben-Haim |
| 2008/0058872 A1 | 3/2008 | Brockway et al. |
| 2008/0058889 A1 | 3/2008 | Ben-Haim |
| 2008/0058891 A1 | 3/2008 | Ben-Haim |
| 2008/0071363 A1 | 3/2008 | Tuval et al. |
| 2008/0119898 A1 | 5/2008 | Ben-David et al. |
| 2008/0119911 A1 | 5/2008 | Rosero |
| 2008/0132972 A1 | 6/2008 | Shuros et al. |
| 2008/0177364 A1 | 7/2008 | Bolea et al. |
| 2008/0195174 A1 | 8/2008 | Walker et al. |
| 2008/0215117 A1* | 9/2008 | Gross ............................. 607/59 |
| 2009/0005859 A1 | 1/2009 | Keilman |
| 2009/0036975 A1 | 2/2009 | Ward et al. |
| 2009/0062874 A1 | 3/2009 | Tracey et al. |
| 2009/0112285 A1 | 4/2009 | Cahan |
| 2009/0198308 A1 | 8/2009 | Gross et al. |
| 2009/0204170 A1 | 8/2009 | Hastings et al. |
| 2009/0228078 A1 | 9/2009 | Zhang et al. |
| 2010/0010556 A1 | 1/2010 | Zhao et al. |
| 2010/0042186 A1 | 2/2010 | Ben-David et al. |
| 2010/0076247 A1 | 3/2010 | Zilbershlag |
| 2010/0094373 A1 | 4/2010 | Sharma |
| 2010/0211131 A1 | 8/2010 | Williams et al. |
| 2010/0305392 A1 | 12/2010 | Gross et al. |
| 2011/0118773 A1 | 5/2011 | Gross |
| 2011/0137370 A1 | 6/2011 | Gross |
| 2012/0035679 A1 | 2/2012 | Dagan |
| 2012/0035711 A1 | 2/2012 | Gross |
| 2012/0158081 A1 | 6/2012 | Gross |
| 2013/0123880 A1 | 5/2013 | Dagan |
| 2013/0338748 A1 | 12/2013 | Dagan |

FOREIGN PATENT DOCUMENTS

| | | |
|---|---|---|
| WO | 0002501 | 1/2000 |
| WO | 2004014456 | 2/2004 |
| WO | WO2005065771 A1 | 7/2005 |
| WO | 2006064503 | 6/2006 |
| WO | 2006094273 | 9/2006 |
| WO | WO2006098928 A1 | 9/2006 |
| WO | 2006123346 | 11/2006 |
| WO | 2007013065 | 2/2007 |
| WO | WO2007013065 A2 | 2/2007 |
| WO | WO-2007064895 | 6/2007 |
| WO | 2007106533 | 9/2007 |

(56) References Cited

FOREIGN PATENT DOCUMENTS

| WO | 2007113818 | 10/2007 |
|---|---|---|
| WO | 2007113833 | 10/2007 |
| WO | WO-2008100390 | 8/2008 |
| WO | WO2009017647 A1 | 2/2009 |
| WO | 2009095918 | 8/2009 |
| WO | 2009095920 | 8/2009 |
| WO | 2012/017437 A1 | 2/2012 |
| WO | 2012/085907 A2 | 6/2012 |
| WO | 2013/035092 A2 | 3/2013 |
| WO | 2013/069020 A1 | 5/2013 |
| WO | 2013/164829 A1 | 11/2013 |

OTHER PUBLICATIONS

An International Preliminary Examination Report on Patentability dated Aug. 12, 2010, which issued during the prosecution of Applicant's PCT/IL09/00115.
MC Frost, et al., "Preparation and characterization of implantable sensors with nitric oxide release coating", Microchemical Journal vol. 74 Issue: 3 Jun. 2003, pp. 277-288.
Gong Z, "Loss of nitric oxide production in the coronary circulation after the development of dilated cardiomyopathy: a specific defect in the neural regulation of coronary blood flow", Clinical and Experimental Pharmacology and Physiology 23(8): 715-721 (1996).
Paulus WJ, "Beneficial effects of nitric oxide on cardiac diastolic function: the flip side of the coin", Heart Failure Review 5(4): 337-344 (2000).
Sherman AJ, :Blockade of nitric oxide synthesis reduces myocardial oxygen consumption in vivo, Circulation 95:1328-1334, 1997.
Kugiyama K, "Nitric oxide activity is deficient in spasm arteries of patients with coronary spastic angina", Circulation 94:266-272, 1996.
Sabbah H. et al., "Global left ventricular remodeling with the Acorn Cardiac Support Device: Hemodynamic and angiographic findings in dogs with heart failure", Heart Failure 10(20: 109-115, 2005 (only first page).
"Improving the Thromboresistivity of Chemical Sensors via Nitric Oxide Release" Fabrication and in Vivo Evaluation of NO-Releasing Oxygen-Sensing Catheters, by MH Schoenfisch et al., Anal. Chem., 72 (6), 1119-1126, 2000.
"Endogenous and Exogenous Nitric Oxide Protect Against Intracoronary Thrombosis and Reocclusion After Thrombolysis," by Sheng-Kun Yao et al., Circulation. 1995;92: 1005-1010.
"Improving the biocompatibility of in vivo sensors via nitric oxide release," by Jae Ho Shin et al., Analyst, 2006, 131, 609-615.
Cheetah Medical Inc. manufactures the Cheetah Reliant, Jan. 23, 2008.
CardioMEMS, Inv., manufactures the EndoSure® Wireless AAA Pressure Measurement System, Nov. 11, 2005.
Sulzer Intra Therapeutics Inc. manufactures the IntraCoil® Self-Expanding Peripheral Stent (IntraCoil® Stent), Jun. 28, 2002.
"Vagus nerve stimulation as a method to temporarily slow or arrest the heart," by Matheny, Ann Thorac Surg. Jun. 1997;63(6 Suppl):S28-9—an abstract.
"Vagus nerve stimulation decreases left ventricular contractility in vivo in the human and pig heart," by Lewis, J Physiol. Jul. 15, 2001; 534(Pt 2): 547-552.
"Sympathovagal balance is major determinant of short-term blood pressure variability in healthy subjects," by Laitinen, Am J Physiol Heart Circ Physiol 276:1245-1252, 1999.
"Optimal frequency ranges for extracting information on cardiovascular autonomic control from the blood pressure and pulse interval spectrograms in mice," by Baudrie, Am J Physiol Regul Integr Comp Physiol 292: R904-R912, 2007.
"Neural influences on cardiovascular variability: possibilities and pitfalls," by Malpas, Am J Physiol Heart Circ Physiol 282: H6-H20, 2002.

"Heart rate variability," by Task Force of the European Society of Cardiology and the North American Society of Pacing and Electrophysiology, European Heart Journal (1996) 17, 354-381.
"Heart rate and vasomotor control during exercise," by Vallais, Proceedings of the 29th Annual International Conference of the IEEE EMBS, Cité Internationale, Lyon, France, Aug. 23-26, 2007.
"Effects of chronic baroreceptor stimulation on the autonomic cardiovascular regulation in patients with drug-resistant arterial hypertension," by Wustmann, Hypertension 2009;54;530-536.
Biosense Webster, Inc. (CA, USA) manufactures the LASSO 2515 Variable Circular Mapping Catheter.
Hayashida at al., Jpn J. Pharmacol. "Comparison of neurogenic conotraction and relaxation in canine corpus cavernosum and penile artery and vein", 72:231-240 (1996) p. 232, col. 2, para 1; p. 238, col. 2, para 2.
An International Search Report and a Written Opinion both dated Jul. 13, 2009, which issued during the prosecution of Applicant's PCT/IL09/00117.
An International Search Report and a Written Opinion both dated May 12, 2009, which issued during the prosecution of Applicant's PCT/IL09/00 115.
Taylor et al., "The unequal influences of the left and right vagi on the control of the heart and pulmonary artery in the rattlesnake, *Crotalus durissus*", The Journal of Experimental Biology 212:145-151 (2008).
Hamilton and Feigl, "Coronary vascular sympathetic beta-receptor innervation", American Journal of Physiology, 230 (6):1569-1576 (1976).
An International Search Report and a Written Opinion both dated Dec. 19, 2011, which issued during the prosecution of Applicant's PCT/IL11/00636.
An Office Action dated Mar. 15, 2012, which issued during prosecution of U.S. Appl. No. 12/792,227.
A Supplementary European search Report dated Dec. 14, 2012, which issued during the prosecution of European Patent Application No. 06766171.
An Office Action dated Oct. 2, 2012, which issued during the prosecution of U.S. Appl. No. 12/851,214.
An English Translation of an Office Action dated Oct. 8, 2012, which issued during the prosecution of Chinese Patent Application No. 200980111617.8.
An Office Action dated Jun. 19, 2012, which issued during the prosecution of U.S. Appl. No. 11/995,904.
An Office Action dated Jul. 18, 2012, which issued during the prosecution of U.S. Appl. No. 13/210,778.
An Office Action dated Aug. 29, 2012, which issued during the prosecution of U.S. Appl. No. 12/792,227.
An Office Action dated Aug. 1, 2012, which issued during the prosecution of U.S. Appl. No. 12/957,799.
An International Search Report and a Written Opinion both dated Jul. 5, 2012, which issued during the prosecution of Applicant's PCT/IL11/00952.
An International Search Report and a Written Opinion both dated Aug. 8, 2013, which issued during the prosecution of Applicant's PCT/IL2013/050375.
An Office Action dated Apr. 25, 2013, which issued during the prosecution of U.S. Appl. No. 11/995,904.
An Office Action dated Apr. 5, 2013, which issued during the prosecution of U.S. Appl. No. 12/792,227.
Supplementary European Search Report for EP Application No. 11814203 dated Nov. 12, 2013.
An Office Action dated Jul. 7, 2014, which issued during the prosecution of U.S. Appl. No. 12/792,227. 5 pages.
An Office Action dated Dec. 20, 2013, which issued during the prosecution of U.S. Appl. No. 12/792,227. 10 pages.
An Office Action dated Dec. 13, 2013, which issued during the prosecution of U.S. Appl. No. 13/294,062, 9 pages.
An Office Action dated Nov. 12, 2013, which issued during the prosecution of U.S. Appl. No. 11/995,904, 18 pages.

* cited by examiner

INTRA-AORTIC ELECTRICAL COUNTERPULSATION

FIELD OF THE INVENTION

The present invention generally relates to implanted medical apparatus. Specifically, the present invention relates to apparatus for enhancing coronary blood flow.

BACKGROUND OF THE INVENTION

Many patients suffer from impaired coronary perfusion, i.e., an inadequate supply of blood, and therefore oxygen, to the heart. Counterpulsation devices increase the blood supply to the heart by increasing blood flow through the coronary arteries, the coronary arteries supplying blood to the heart.

PCT Publication WO 07/013,065 to Gross, which is incorporated herein by reference, describes apparatus, including a bifurcation stent comprising one or more electrodes, the stent configured to be placed in a primary passage and a secondary passage of a blood vessel, and a control unit, configured to drive the electrodes to apply a signal to a wall of the blood vessel, and to configure the signal to increase nitric oxide (NO) secretion by the wall.

In an embodiment described in the '065 publication, a counterpulsation device is inserted in an ascending aorta of a subject. The counterpulsation device comprises one or more electrodes, and an implantable or external control unit. The control unit is described as being adapted to drive the electrodes to apply an electrical signal to a wall of the ascending aorta during systole, and to configure the signal to induce an increase in NO secretion by the wall. The increased NO secretion dilates the wall such that during systole the wall stores energy, and pressure on the heart is reduced. During diastole, the wall is described as constricting, releasing the stored energy and thereby increasing blood pressure and coronary blood flow. The control unit is described as being additionally configured to drive electrodes to apply, during diastole, stimulation configured to enhance the rapid constriction of aorta.

PCT Publication WO 07/113,818 to Cahan et al., which is incorporated herein by reference, describes an implantable artificial pacemaker (AAP) comprising oscillatory means providing pulsating signals at a pre-selected frequency, wherein the pacemaker is pacing the aorta. The application also describes an AAP further comprising: (i) a plurality of sensors disposed internally or externally to the aorta; and (ii) a pacing means in which the AAP stimulates the aortic media, augmenting physiological aortic elastic recoil. An AAP further comprising a processor capable of obtaining information from sensors and triggering an appropriate contraction wave in the aortic media is also described. A method of managing aortic rhythm is also described, comprising: (i) implanting an AAP comprising oscillatory means; and (ii) pulsating signals at a preselected frequency, so as to pace the aorta and in which the pulsating signals are provided by synchronizing and coordinating activation impulses in a portion of the aorta using electrical impulses.

US Patent Application Publication 2007/0150009 to Kveen et al., which is incorporated herein by reference, describes apparatus, systems, and methods that include a pacing apparatus having a stent electrode through which pulses of electrical current can be delivered. Stent electrodes are described as receiving energy for generating the electrical current from a variety of sources. Sources include one or more induction coils that can form at least a portion of the stent. Sources also include an implantable pulse generator coupled to a lead through which pulses of the electrical current are supplied to the stent electrodes.

U.S. Pat. No. 6,865,416 to Dev et al., which is incorporated herein by reference, describes methods for inducing or increasing the vasodilation of a vessel. The patent further provides methods for inducing or increasing the flow of fluid through a vessel. An electrical impulse is applied to the vessel in order to induce or increase vessel vasodilation or to induce or increase the flow of fluid through the vessel. The '416 patent states:

"Although not wishing to be bound by any particular theory, the induction or increase of vessel vasodilation by an electrical impulse appears to result either from a direct effect caused by the electrical current applied to the vessel, or an indirect effect resulting from the release or stimulation of factors that promote vasodilation, such as the release of endothelium derived relaxation factors (EDRF) currently identified as nitric oxide (NO) or other vasodilating substances triggered by the electrical pulses applied to the cells of the vessel."

US Patent Application Publication 2004/0106954 to Whitehurst et al., which is incorporated herein by reference, describes a treatment of congestive heart failure (CHF) that includes implantation of the discharge portion(s) of a catheter and, optionally, electrode(s) on a lead, near the tissue(s) to be stimulated. Stimulation pulses, i.e., drug infusion pulses and optional electrical pulses, are supplied by a stimulator implanted remotely, and through the catheter or lead, which is tunneled subcutaneously between the stimulator and stimulation site. Stimulation sites include the coronary arteries, the aorta, the left ventricle, the left atrium, and/or the pulmonary veins, among other locations. Disclosed treatments include drugs used for acute treatment of CHF, for chronic treatment of CHF, and drugs to reverse CHF. In an embodiment described in the '954 publication, when catheters and/or electrodes of a stimulator are implanted, for example, in and/or near the left coronary artery or its branches, signals from an ECG sensor built into the stimulator are described as being used to adjust stimulation parameters.

US Patent Application Publication 2004/0054384 to Nachum, which is incorporated herein by reference, describes a treatment method and device for promoting a localized increase in the flow of blood through a blood vessel in an area of the body, the method including the steps of: (a) providing a system including: (i) at least a first electrode operatively contacting a first portion of body tissue; (ii) at least a second electrode operatively contacting a second portion of body tissue; and (iii) a signal generator, operatively connected to the first electrode and the second electrode, for providing a plurality of electrical impulses to the electrodes; (b) applying the electrical impulses so as to subject the muscular tissue to at least one voltage differential, thereby inducing repeated, contracting, directional movement of muscular tissue associated within the blood vessel, so as to produce a localized increase in the flow of blood through the blood vessel.

Sulzer IntraTherapeutics Inc. manufactures the IntraCoil® Self-Expanding Peripheral Stent (IntraCoil® Stent), which is described as a flexible coil-shaped metallic device that is used in the femoral and popliteal arteries in the leg to hold open areas that were blocked by atherosclerotic disease.

CardioMEMS, Inc., manufactures the EndoSure® Wireless AAA Pressure Measurement System, which is composed of two components: a miniaturized, wireless implantable sensor and an external electronics module. The external electronics module is described as wirelessly communicating with the sensors to deliver patient data. The wireless sensors are described as being powered by RF energy transmitted from an external electronics module and transmitting real-time data without batteries.

Cheetah Medical Inc. manufactures the Cheetah Reliant, which is described as providing continuous tracking of cardiac output and other parameters of cardiac function such as ventricular ejection time and heart rate.

The following patents and patent applications, which are incorporated herein by reference, may be of interest:

U.S. Pat. No. 5,324,323 to Bui
U.S. Pat. No. 5,906,641 to Thompson et al.
U.S. Pat. No. 6,058,331 to King
U.S. Pat. No. 6,086,527 to Talpade
U.S. Pat. No. 6,200,259 to March
U.S. Pat. No. 6,245,103 to Stinson
U.S. Pat. No. 6,347,247 to Dev et al.
U.S. Pat. No. 6,463,323 to Conrad-Vlasak et al.
U.S. Pat. No. 6,485,524 to Strecker
U.S. Pat. No. 6,810,286 to Donovan et al.
U.S. Pat. No. 6,824,561 and US Patent Application Publication 2004/0039417 to Soykan et al.
U.S. Pat. No. 6,845,267 to Harrison et al.
U.S. Pat. No. 6,871,092 to Piccone
U.S. Pat. No. 6,939,345 to KenKnight et al.
U.S. Pat. No. 7,206,637 to Salo
U.S. Pat. No. 7,229,403 to Schock et al.
US 2002/0103454 to Sackner et al.
US 2003/0036773 to Whitehurst et al.
US 2003/0204206 to Padua et al.
US 2006/0276844 to Alon et al. US 2007/0196428 to Glauser et al.
US 2007/0248676 to Stamler et al.
PCT Publication WO 00/002501 to Benjamin et al.
PCT Publication WO 04/014456 to Allen et al.
PCT Publication WO 06/094273 to White et al.
PCT Publication WO 07/106,533 to Stern et al.
PCT Publication WO 07/113,833 to Cahan et al.
PCT Publication WO 2006/064503 to Belsky et al.
PCT Publication WO 2006/123346 to Alon et al.
European Patent Application Publication EP 0 109 935 A1 to Charmillot et al.

SUMMARY OF THE INVENTION

In some embodiments of the present invention, a sensing electrode is implanted at a non-cardiac site in a vicinity of an aorta of a subject. The sensing electrode detects an electrical parameter of the subject's aorta, and a control unit receives the detected parameter and generates an output in response to the detected parameter.

Typically, the electrode is implanted at a site that is between 20 mm and 50 mm distal to an aortic valve of the subject. (In the context of the present patent application and in the claims, the term "distal to" means a site that is distal with respect to the subject's heart.)

In some embodiments, the control unit detects the subject's cardiac cycle, and/or a timing parameter of the subject's blood pressure by analyzing the detected parameter. For some applications, the control unit drives a current into the aorta in response to the detected parameter. In some embodiments, the control unit drives the current in coordination with the subject's cardiac cycle. In some embodiments, the subject's cardiac cycle is determined by analyzing the detected parameter, as described hereinabove. Alternatively, the cardiac cycle is detected using an ECG, and/or by taking impedance measurements, for example, using the Cheetah Reliant, described hereinabove and/or similar technology. For example, in response to detecting systole of the subject, the control unit may dilate the aorta by increasing nitric oxide (NO) secretion by the wall of the aorta by driving the current. Alternatively or additionally, in response to detecting diastole of the subject, the control unit enhances constriction of the aorta by driving the current.

In some embodiments of the present invention, two or more electrodes are implanted in a vicinity of an aorta of a subject. A control unit peristaltically pumps blood through the aorta by sequentially dilating portions of the aorta by facilitating nitric oxide production by the aorta by driving a current into the aorta via the electrodes.

In some embodiments, the control unit receives an indication of the subject's cardiac cycle (e.g., using techniques described herein), and drives the current in coordination with the subject's cardiac cycle. Typically, the control unit peristaltically pumps blood through the aorta during systole of the subject. In some embodiments, during diastole of the subject, the control unit does not peristaltically pump blood through the aorta, and/or the control unit enhances constriction of the aorta by driving a diastolic current into the aorta via the electrodes.

There is therefore provided in accordance with an embodiment of the invention apparatus, including:

a sensing electrode configured to be implanted at a non-cardiac site in a vicinity of an aorta of a subject and to detect an electrical parameter of the aorta; and a control unit configured to receive the detected parameter and to generate an output in response to the detected parameter.

In an embodiment, the sensing electrode is configured to be implanted at a site selected from the group consisting of: an ascending aorta of the subject, an aortic arch of the subject, and a descending aorta of the subject.

In an embodiment, the control unit is configured to be powered by being irradiated with electromagnetic radiation from outside a body of the subject.

In an embodiment, the control unit is configured to be powered by being irradiated with ultrasound radiation from outside a body of the subject.

In an embodiment, the control unit is configured to be disposed in a vicinity of the subject's aorta.

In an embodiment, the control unit is configured to be disposed inside a body of the subject.

In an embodiment, the control unit is configured to be disposed outside a body of the subject.

In an embodiment, the electrode is configured to be placed inside the aorta.

In an embodiment, the electrode is configured to be placed outside the aorta.

In an embodiment, the electrode is configured to be placed in a wall of the aorta.

In an embodiment, the electrode includes at least two electrodes, and one of the at least two electrodes is configured to be placed inside the aorta, and another electrode of the at least two electrodes is configured to be placed outside the aorta.

In an embodiment, the electrode includes at least a first electrode and a second electrode, the first and second electrodes being configured to be placed within the aorta at a longitudinal distance from each other of between 10 mm and 30 mm.

In an embodiment, the electrode includes at least a first electrode and a second electrode, the first and second electrodes being configured to be placed at a radial distance from each other of less than 10 degrees.

In an embodiment, the electrode is configured to be implanted at a site that is between 20 mm and 50 mm distal to an aortic valve of the subject.

In an embodiment, the apparatus further includes an intra-aortic balloon pump configured to be implanted in the subject's aorta, and the control unit is configured to pump the intra-aortic balloon pump in response to the detected parameter.

In an embodiment, the control unit is configured to detect a cardiac cycle of the subject by analyzing the detected parameter.

In an embodiment, the control unit is configured to detect a timing parameter of blood pressure of the subject by receiving the detected parameter.

In an embodiment, the control unit is configured to detect an indication of an ECG of the subject by receiving the detected parameter.

In an embodiment, the electrode includes at least a first electrode configured to be placed in an ascending aorta of the subject, and at least a second electrode configured to be placed in a descending aorta of the subject.

In an embodiment, the electrode includes ten or more electrodes.

In an embodiment, the sensing electrode is configured to be disposed having a surface area of between 3 square mm and 15 square mm in contact with tissue of the aorta.

In an embodiment, the sensing electrode is configured to be disposed having a surface area of between 8 square mm and 12 square mm in contact with tissue of the aorta.

In an embodiment, the control unit is configured to drive a current into a heart of the subject in response to the detected parameter.

In an embodiment, the control unit is configured to defibrillate the subject's heart by driving the current into the subject's heart.

In an embodiment, the control unit is configured to drive a current into the aorta in response to the detected parameter.

In an embodiment, the control unit is configured to drive the current into the aorta via the sensing electrode.

In an embodiment, the control unit is configured to drive the current independently of a cardiac cycle of the subject.

In an embodiment, the apparatus further includes a driving electrode, and the control unit is configured to drive the current into the aorta via the driving electrode.

In an embodiment, the driving electrode includes at least a first electrode configured to be placed in an ascending aorta of the subject, and at least a second electrode configured to be placed in a descending aorta of the subject.

In an embodiment, the driving electrode includes ten or more electrodes.

In an embodiment, the driving electrode includes at least two electrodes, and one of the at least two electrodes is configured to be placed inside the aorta, and another electrode of the two or more electrodes is configured to be placed outside the aorta.

In an embodiment, the driving electrode includes at least a first and a second electrode, and the first and second electrodes are configured to be placed within the aorta at a longitudinal distance from each other of between 10 mm and 30 mm.

In an embodiment, the driving electrode includes at least a first and a second electrode, and the first and second electrodes are configured to be placed within the aorta at a radial distance from each other of less than 10 degrees.

In an embodiment, the driving electrode is configured to be placed between 10 and 50 mm distal to an aortic valve of the subject.

In an embodiment, the driving electrode is configured to be disposed having a surface area of between 3 square mm and 15 square mm in contact with tissue of the aorta.

In an embodiment, the driving electrode is configured to be disposed having a surface area of between 5 square mm and 12 square mm in contact with tissue of the aorta.

In an embodiment, the control unit is configured to detect a cardiac cycle of the subject by receiving the detected parameter, and is configured to drive the current in coordination with the subject's cardiac cycle.

In an embodiment, the control unit is configured to dilate the aorta by increasing nitric oxide (NO) secretion by the wall of the aorta by applying the current.

In an embodiment, the control unit is configured to dilate the aorta in response to detecting an indication of systole of the subject.

In an embodiment, the control unit is configured to dilate the aorta by configuring the current to have a frequency of between 5 Hz and 20 Hz.

In an embodiment, the control unit is configured to dilate the aorta by configuring the current to have a frequency of between 10 Hz and 15 Hz.

In an embodiment, the control unit is configured to dilate the aorta by configuring the current to have an amplitude of between 1 mA and 5 mA.

In an embodiment, the control unit is configured to dilate the aorta by configuring the current to have an amplitude of between 2 mA and 3 mA.

In an embodiment, the control unit is configured to dilate the aorta by configuring the current to have two pulses to eight pulses per cardiac cycle of the subject.

In an embodiment, the control unit is configured to dilate the aorta by configuring the current to have three pulses to five pulses per cardiac cycle of the subject.

In an embodiment, the control unit, in response to detecting an indication of diastole of the subject, is configured to enhance constriction of the aorta by driving the current.

In an embodiment, the control unit is configured to enhance constriction of the aorta by configuring the current to have a frequency of between 40 Hz and 70 Hz.

In an embodiment, the control unit is configured to enhance constriction of the aorta by configuring the current to have an amplitude of between 5 mA and 20 mA.

In an embodiment, the control unit is configured to constrict the aorta by configuring the current to have an amplitude of between 8 mA and 15 mA.

In an embodiment, the control unit is configured to enhance constriction of the aorta by configuring the current to have ten pulses to twenty pulses per cardiac cycle.

In an embodiment, the control unit is configured to enhance constriction of the aorta by configuring the current to have thirteen pulses to seventeen pulses per cardiac cycle.

In an embodiment, the control unit,
in response to detecting systole of the subject, is configured to dilate the aorta by increasing nitric oxide (NO) secretion by the wall of the aorta by driving the current, and
in response to detecting diastole of the subject, is configured to enhance constriction of the aorta by driving the current.

In an embodiment, the control unit is configured to dilate the aorta during every systole, and is configured to enhance constriction of the aorta during intermittent diastoles.

In an embodiment, the control unit is configured to dilate the aorta during intermittent systoles, and is configured to enhance constriction of the aorta during every diastole.

In an embodiment, the control unit is configured to dilate the aorta during intermittent systoles, and is configured to enhance constriction of the aorta during intermittent diastoles.

In an embodiment, the apparatus further includes a self-expansible stent, and the electrode is configured to be disposed on the self-expansible stent, and to be implanted inside the aorta while disposed on the self-expansible stent.

In an embodiment, the apparatus further includes a catheter,
- the stent is configured to be inserted into the aorta via the catheter,
- the stent is configured to be in a contracted state when it is inside the catheter, and
- the stent is configured to expand inside the aorta upon exiting the catheter.

In an embodiment, the stent has a figure-of-eight shape.

In an embodiment, the stent includes a coil.

In an embodiment, the stent includes two or more spirals.

In an embodiment, the control unit is configured to extract energy from a body of the subject, and to facilitate the detection of the electrical parameter of the aorta using the extracted energy.

In an embodiment, the control unit is configured to extract the energy from a flow of blood through the aorta.

In an embodiment, the control unit is configured to extract the energy from gastric acid of the subject.

There is additionally provided in accordance with an embodiment of the invention, apparatus, including:
- two or more electrodes configured to be implanted in a vicinity of an aorta of a subject; and
- a control unit configured to peristaltically pump blood through the aorta by sequentially dilating portions of the aorta by facilitating nitric oxide production by the aorta by driving a current into the aorta via the electrodes.

In an embodiment, at least one of the electrodes is configured to be implanted at a site selected from the group consisting of: an ascending aorta of the subject, an aortic arch of the subject, and a descending aorta of the subject.

In an embodiment, the control unit is configured to peristaltically pump the blood independently of a cardiac cycle of the subject.

In an embodiment, the control unit is configured to be disposed in a vicinity of the subject's aorta.

In an embodiment, the control unit is configured to be disposed inside a body of the subject.

In an embodiment, the control unit is configured to be disposed outside a body of the subject.

In an embodiment, the electrodes are configured to be placed inside the aorta.

In an embodiment, the electrodes are configured to be placed outside the aorta.

In an embodiment, the electrodes are configured to be placed in a wall of the aorta.

In an embodiment, one of the two or more electrodes is configured to be placed inside the aorta, and another electrode of the two or more electrodes is configured to be placed outside the aorta.

In an embodiment, the two or more electrodes are configured to be placed within the aorta at a longitudinal distance from each other of between 10 mm and 30 mm.

In an embodiment, the two or more electrodes are configured to be placed within the aorta at a radial distance from each other of less than 10 degrees.

In an embodiment, the electrodes are configured to be placed between 10 and 50 mm distal to an aortic valve of the subject.

In an embodiment, the electrodes include at least a first electrode configured to be placed in an ascending aorta of the subject, and at least a second electrode configured to be placed in a descending aorta of the subject.

In an embodiment, the electrodes include ten or more electrodes.

In an embodiment, the control unit is configured to dilate the portions of the aorta by configuring the current to have a frequency of between 5 Hz and 20 Hz.

In an embodiment, the control unit is configured to dilate the portions of the aorta by configuring the current to have a frequency of between 10 Hz and 15 Hz.

In an embodiment, the control unit is configured to dilate the portions of the aorta by configuring the current to have an amplitude of between 1 mA and 5 mA.

In an embodiment, the control unit is configured to dilate the portions of the aorta by configuring the current to have an amplitude of between 2 mA and 3 mA.

In an embodiment, the control unit is configured to dilate the portions of the aorta by configuring the current to have two pulses to eight pulses per cardiac cycle.

In an embodiment, the control unit is configured to dilate the portions of the aorta by configuring the current to have three pulses to five pulses per cardiac cycle.

In an embodiment, each of the electrodes is configured to be disposed having a surface area of between 3 square mm and 15 square mm in contact with tissue of the aorta.

In an embodiment, each of the electrodes is configured to be disposed having a surface area of between 5 square mm and 12 square mm in contact with tissue of the aorta.

In an embodiment, the control unit is configured to receive an indication of a cardiac cycle of the subject, and is configured to drive the current in coordination with the subject's cardiac cycle.

In an embodiment, the control unit is configured to peristaltically pump blood through the aorta during systole of the subject.

In an embodiment, the control unit is additionally configured to peristaltically pump blood through the aorta by sequentially constricting portions of the aorta by driving a further current into the aorta via the electrodes during systole.

In an embodiment, during diastole of the subject the control unit is configured:
- not to peristaltically pump blood through the aorta, and
- to enhance constriction of the aorta by driving a diastolic current into the aorta via the electrodes.

In an embodiment, the control unit is configured to peristaltically pump blood through the aorta by enhancing constriction of the aorta.

In an embodiment, the control unit is configured to enhance constriction of the aorta by configuring the diastolic current to have a frequency of between 40 Hz and 70 Hz.

In an embodiment, the control unit is configured to enhance constriction of the aorta by configuring the diastolic current to have an amplitude of between 5 mA and 20 mA.

In an embodiment, the control unit is configured to enhance constriction of the aorta by configuring the diastolic current to have an amplitude of between 8 mA and 15 mA.

In an embodiment, the control unit is configured to enhance constriction of the aorta by configuring the diastolic current to have ten pulses to twenty pulses per cardiac cycle.

In an embodiment, the control unit is configured to enhance constriction of the aorta by configuring the diastolic current to have thirteen pulses to seventeen pulses per cardiac cycle.

In an embodiment, the control unit is configured to peristaltically pump blood through the aorta during every systole, and is configured to enhance constriction of the aorta during intermittent diastoles.

In an embodiment, the control unit is configured to peristaltically pump blood through the aorta during intermittent systoles, and is configured to enhance constriction of the aorta during every diastole.

In an embodiment, the control unit is configured to peristaltically pump blood through the aorta during intermittent systoles, and is configured to enhance constriction of the aorta during intermittent diastoles.

In an embodiment, the apparatus further includes a self-expansible stent, and the electrodes are configured to be disposed on the self-expansible stent, and to be implanted inside the aorta while disposed on the self-expansible stent.

In an embodiment, the apparatus further includes a catheter
the stent is configured to be inserted into the aorta via the catheter,
the stent is configured to be in a contracted state when it is inside the catheter, and
the stent is configured to expand inside the aorta upon exiting the catheter.

In an embodiment, the stent has a figure-of-eight shape.
In an embodiment, the stent includes a coil.
In an embodiment, the stent includes two or more spirals.

There is additionally provided in accordance with an embodiment of the invention, a method, including:
detecting a parameter of an electrical current of an aorta of a subject; and
treating the subject in response to generating an output in response to the detected parameter.

There is additionally provided in accordance with an embodiment of the invention, a method, including:
identifying a subject who would benefit from increased aortic blood flow; and
peristaltically pumping blood of the subject through the aorta by sequentially dilating portions of the aorta by facilitating nitric oxide production by the aorta by driving a current into the aorta.

The present invention will be more fully understood from the following detailed description of embodiments thereof, taken together with the drawings, in which:

DETAILED DESCRIPTION OF EMBODIMENTS

Figure 1:
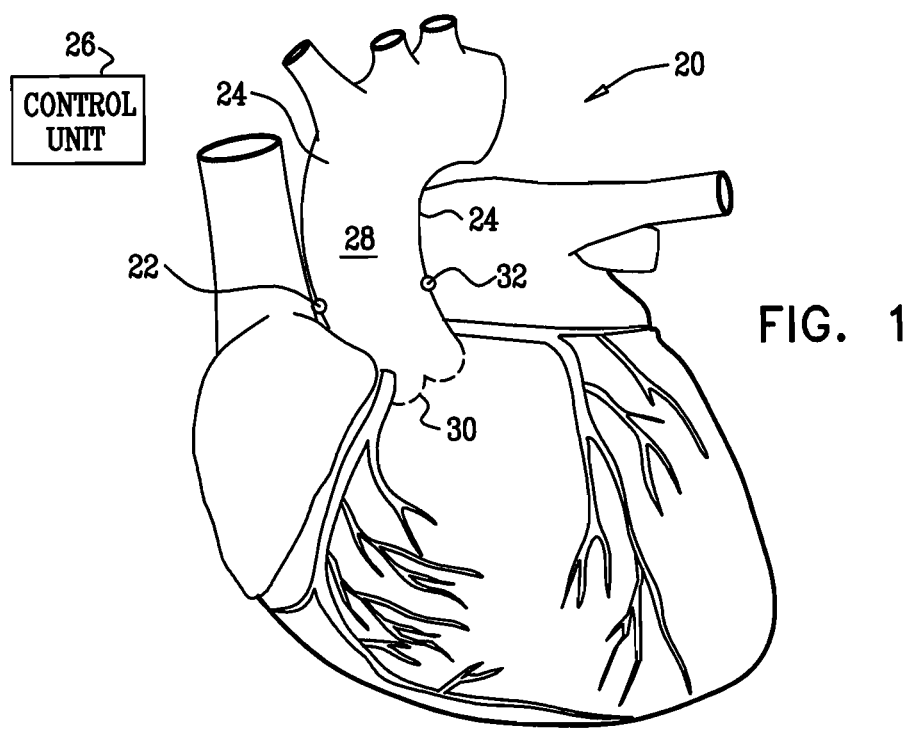
FIG. 1 is a schematic illustration of an electrode implanted in a non-cardiac site in a vicinity of a subject's aorta, in accordance with an embodiment of the present invention.

Reference is now made to FIG. 1, which is a schematic illustration of apparatus 20, comprising at least one electrode 22 implanted at a non-cardiac site in a vicinity of a subject's aorta 24, in accordance with an embodiment of the present invention. In some embodiments, electrode 22 detects an electrical parameter of the subject's aorta, and a control unit 26 receives the detected parameter and generates an output in response to the detected parameter.

In some embodiments, control unit 26 is disposed inside the subject's body, e.g., in a vicinity of the subject's aorta 24, or remote therefrom, similar to the implanted pulse generator of a standard cardiac pacemaker. Alternatively, the control unit is disposed outside the subject's body.

In some embodiments, electrode 22 is disposed inside the aorta. Alternatively or additionally, the electrode is disposed in a non-cardiac site in a vicinity of the aorta, and/or in a wall of the aorta. For some applications, at least two electrodes 22 are implanted in the subject. One of the electrodes is placed inside the aorta, and another of the electrodes is placed outside the aorta. In some embodiments, first and second electrodes 22 are placed within the aorta at a longitudinal distance from each other of between 10 mm and 30 mm and/or at a radial distance from each other of less than 10 degrees. In some embodiments, one or more electrodes 22 are placed in the subject's ascending aorta and one or more electrodes are placed in the subject's aortic arch and/or descending aorta. In some embodiments ten or more electrodes, for example 20 electrodes are implanted inside the aorta. Typically, electrode 22 is implanted in a site of the ascending aorta at a site that is between 20 to 50 mm distal to an aortic valve 30 of the subject.

In some embodiments, control unit 26 detects the subject's cardiac cycle, and/or a timing parameter of the subject's blood pressure by analyzing the detected parameter. For some applications, the control unit drives a current into the aorta in response to the detected parameter. Examples of such detecting and current application are described hereinbelow.

For some applications, the control unit drives the current in coordination with the subject's cardiac cycle. Alternatively, control unit 26 drives a current into the subject's aorta independently of the subject's cardiac cycle.

In some embodiments, the control unit drives the current into the aorta via sensing electrode 22. Alternatively or additionally, apparatus 20 comprises one or more additional driving electrodes 32, and the control unit drives the current into the aorta via the driving electrodes. Typically, the placement parameters of the driving electrodes are similar to those described hereinabove, with respect to sensing electrode(s) 22. In some embodiments, the driving electrodes are oriented to have a surface area of between 3 square mm and 15 square mm, e.g. between 5 square mm and 12 square mm, in contact with tissue of the aorta.

In some embodiments, control unit 26, by driving a current into the aorta, dilates the aorta by increasing nitric oxide (NO) secretion by the wall of the aorta. Typically, the control unit dilates the aorta in response to detecting an indication of systole of the subject. In some embodiments, dilating the aorta during systole reduces the left ventricular afterload of the subject, and thereby increases the subject's stroke volume and/or ejection fraction. Alternatively, the aorta may be dilated during systole for a different purpose.

In some embodiments, the control unit dilates the aorta by configuring the current to have a frequency of between 5 Hz and 20 Hz, e.g., between 10 Hz and 15 Hz. For some applications, the current has an amplitude of between 1 mA and 5 mA, e.g., between 2 mA and 3 mA. In some embodiments, a current having two pulses to eight pulses, e.g., three pulses to five pulses, per cardiac cycle, is driven into the aorta to dilate the aorta.

In some embodiments, control unit 26 enhances constriction of the aorta by driving a current into the aorta. For example, the control unit may enhance constriction of the aorta in response to the control unit detecting an indication of diastole of the subject. For some applications, enhancing constriction of the aorta during diastole elevates diastolic blood pressure, thereby increasing coronary perfusion, and/or the supply of blood to organs of the subject's body other than the heart. Alternatively, constriction of the aorta may be enhanced during diastole for a different purpose.

In some embodiments, the control unit enhances constriction of the aorta by driving a current having a frequency of between 40 Hz and 70 Hz. For some applications, the current has an amplitude of between 5 mA and 20 mA, e.g., between 8 mA and 15 mA. In some embodiments, a current having ten pulses to twenty pulses, e.g., thirteen pulses to seventeen pulses, per cardiac cycle, is driven into the aorta to enhance constriction of the aorta.

In some embodiments, control unit 26, (a) in response to detecting systole of the subject, dilates the aorta by increasing nitric oxide (NO) secretion by the wall of the aorta by driving a current into the aorta, and (b) in response to detecting a diastole of the subject, enhances constriction of the aorta by driving a current into the aorta. In some embodiments, the control unit dilates the aorta during every systole, and enhances constriction of the aorta during intermittent diastoles. Alternatively, the control unit dilates the aorta during intermittent systoles, and enhances constriction of the aorta during every diastole. Further alternatively, the control unit dilates the aorta during every systole, and enhances constriction of the aorta during every diastole. Typically, a suitable protocol is selected based on the medical condition of the subject.

Figure 2A:
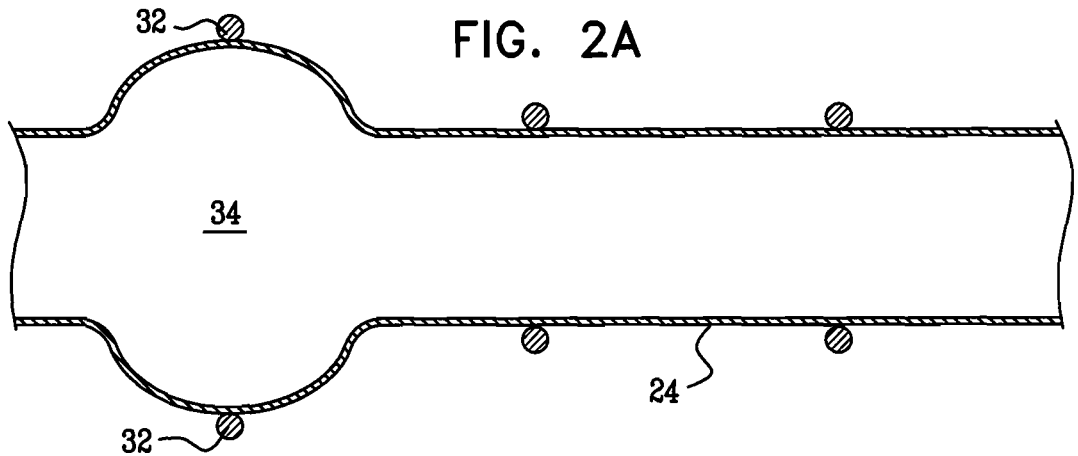
FIGS. 2A-C are schematic illustrations of peristaltic dilation of the aorta, in accordance with an embodiment of the present invention.
Figure 2B:
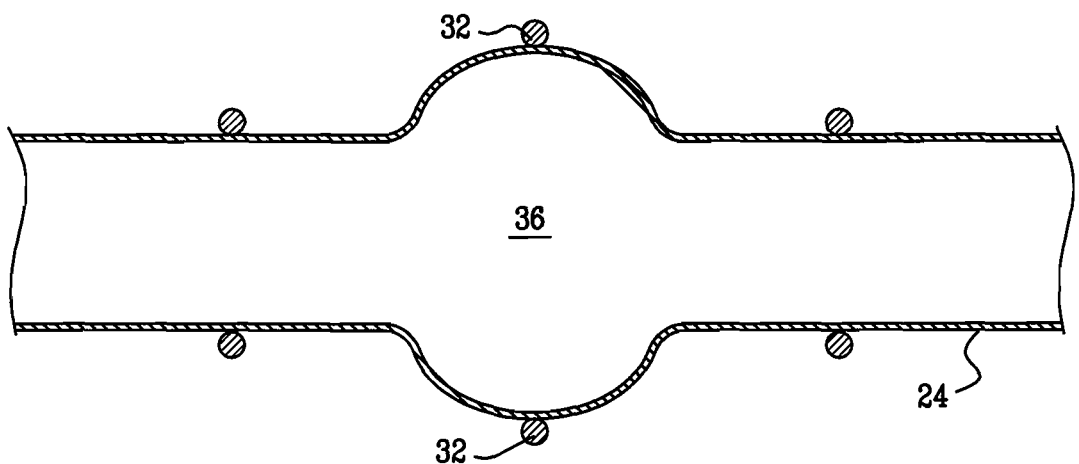
Figure 2C:
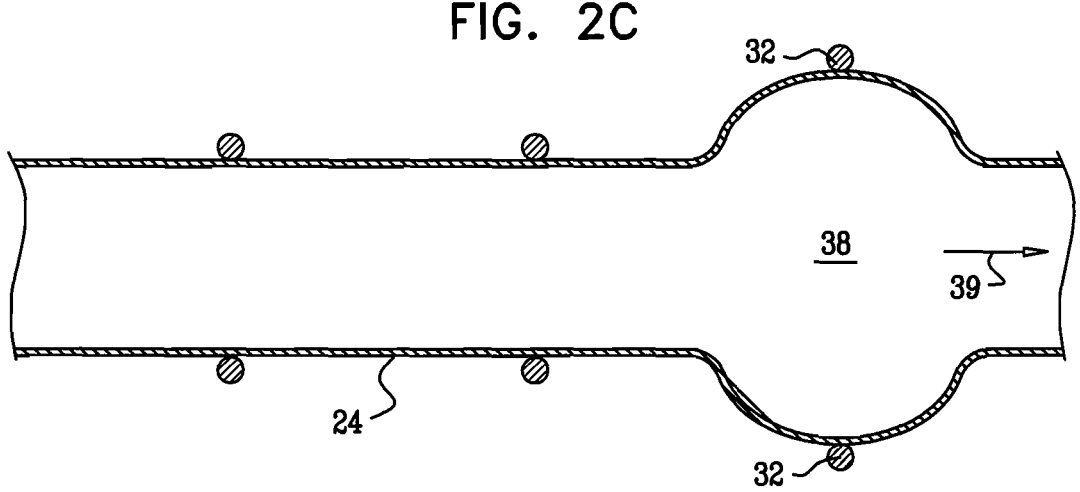

Reference is now made to FIGS. 2A-C, which are schematic illustrations of peristaltic dilation of aorta 24, in accordance with an embodiment of the present invention. In some embodiments of the invention, control unit 26 peristaltically pumps blood through the aorta by sequentially dilating portions of the aorta by facilitating nitric oxide production by the aorta by driving a current into the aorta via two or more electrodes disposed at respective longitudinal positions on the aorta. Typically, during diastole, control unit 26 (FIG. 1) causes a region 34 of the aorta to dilate by driving a current through the distal-most electrodes of electrodes 32 (as shown in FIG. 2A). The current is sequentially driven through the remaining electrodes, causing regions 36 and 38 to dilate (as shown in FIGS. 2B and 2C respectively), and causing blood to flow in a proximal direction, in the direction of arrow 39, to enhance coronary artery perfusion. Alternatively, peristalsis generated as described is used to generate distally-directed enhanced blood flow.

Typically, the parameters of the current for dilating the aorta, are as described hereinabove. Typically, the parameters of the electrodes (i.e., the number and spacing of the electrodes) are as described hereinabove. Further typically, the electrodes are configured to induce dilation with a spacing in time of 10 ms to 50 ms. For some applications, the electrodes are disposed longitudinally along the aorta with a longitudinal spacing therebetween of 150%-250% of the local diameter of the aorta and/or of 1-5 cm. The spacing may be maintained, for example, by a housing to which the electrodes are coupled (e.g., a flexible stent) or by sutures or adhesives which couple the electrodes to the aorta. As appropriate for the level of peristaltic flow desired, the time for a peristaltic wave to be generated and to travel from the most distal to the most proximal electrode (or in the opposite direction) typically ranges from 0.25 second to about 2 seconds.

In some embodiments, control unit 26 receives an indication of the subject's cardiac cycle (e.g., via sensing electrode 22), and peristaltically pumps blood in the aorta by driving the current in coordination with the subject's cardiac cycle. In an embodiment, the control unit peristaltically pumps blood through the aorta during systole of the subject. In an embodiment, a peristaltic wave of constriction of the aorta is generated as well as the peristaltic wave of dilation described hereinabove. The peristaltic wave of constriction is behind the peristaltic wave of dilation, and pushes the blood in the peristaltic wave of dilation. For example, while region 36 of the aorta is dilated (as shown in FIG. 2B), region 34 is constricted (constriction not shown), and subsequently, while region 38 is dilated, region 36 is constricted.

In some embodiments, during diastole of the subject, control unit 26 (a) does not peristaltically pump blood through the aorta, and/or (b) enhances constriction of the aorta by driving a diastolic current into the aorta via the electrodes. Typically, the parameters of the diastolic current for enhancing constriction of the aorta are as described hereinabove.

In some embodiments, control unit 26 peristaltically pumps blood proximally during diastole by generating a proximally-directed peristaltic wave of dilation and/or contraction using the techniques described hereinabove.

In some embodiments, control 26 unit peristaltically dilates the aorta during intermittent or all systoles, and/or enhances constriction of the aorta during intermittent or all diastoles.

Typically, control unit 26 comprises a battery. Alternatively, the control unit is powered wirelessly, e.g., by being irradiated with electromagnetic radiation, and/or ultrasound radiation from outside the subject's body, or by extracting energy from the subject's body. For example, the control unit may be disposed inside the subject's aorta, and configured to extract energy from the flow of blood through the aorta. Alternatively or additionally, the control unit may extract energy from the subject's gastric acid.

Figure 3:
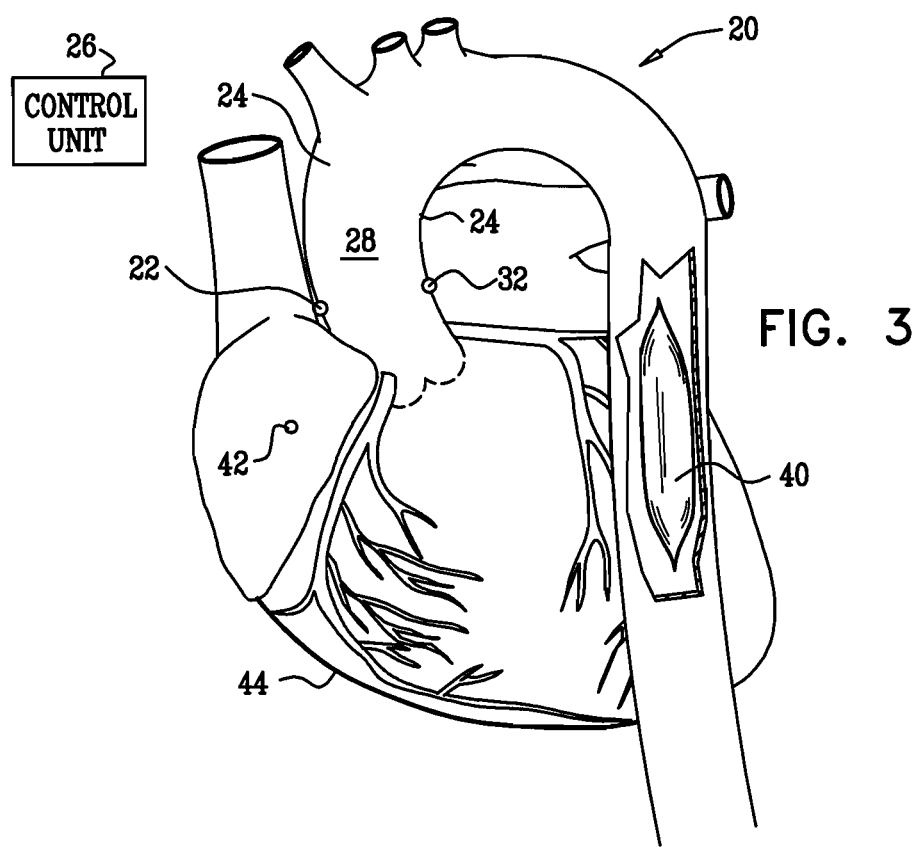
FIG. 3 is a schematic illustration of a control unit configured to generate an output in response to a detected aortic electrical parameter, in accordance with an embodiment of the present invention.

Reference is now made to FIG. 3, which is a schematic illustration of apparatus 20, in accordance with an embodiment of the present invention. In this embodiment, an intra-aortic balloon pump 40 is implanted in a subject's aorta. Control unit 26 pumps the intra-aortic balloon pump in response to the electrical parameter of the aorta that is detected by electrode 22.

For some applications, in addition to or instead of pump 40, apparatus 20 includes at least one cardiac electrode 42 implanted in a vicinity of the subject's heart 44. Control unit 26 drives a current into the subject's heart, via the cardiac electrode, in response to the electrical parameter of the aorta that is detected by sensing electrode 22. In some embodiments, the control unit defibrillates or cardioverts the subject's heart by driving the current into the subject's heart, in response to aortic sensing, and/or in response to sensing on the heart.

Figure 4A:
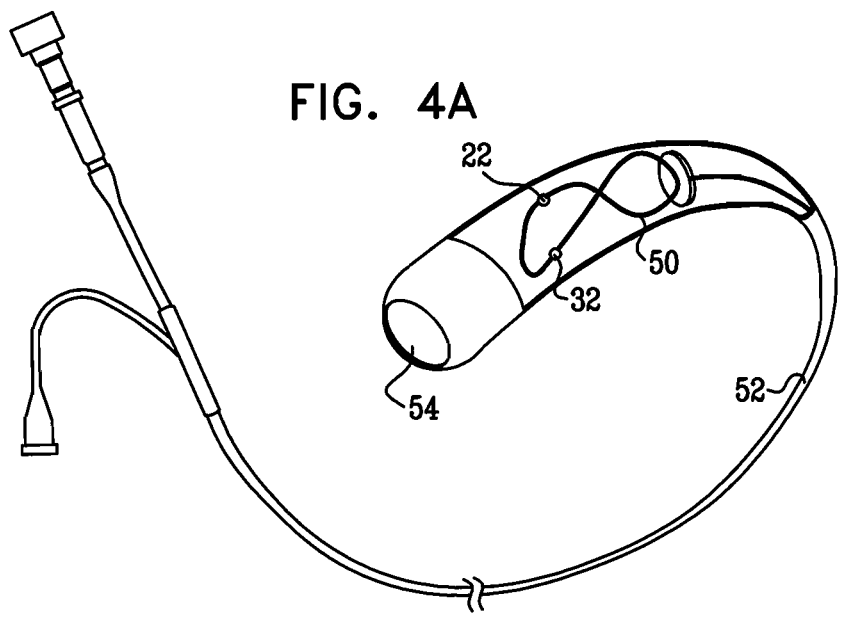
FIGS. 4A-B are schematic illustrations of electrodes disposed on a self-expansible stent, in accordance with an embodiment of the present invention.
Figure 4B:
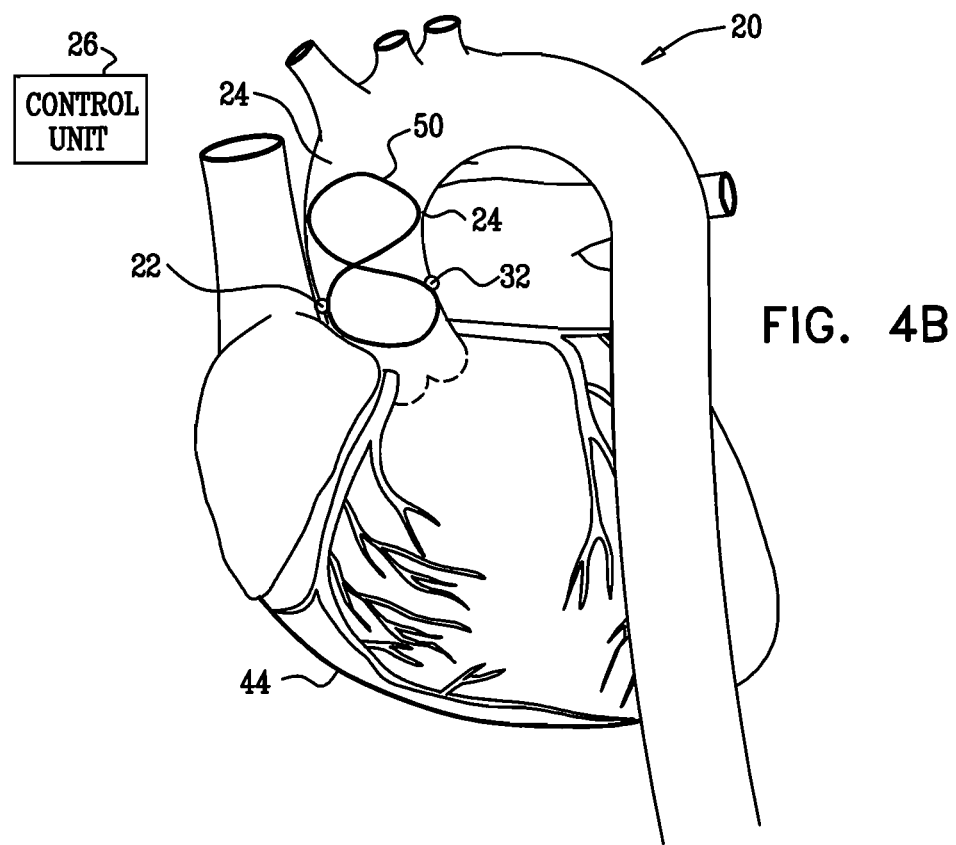

Reference is now made to FIGS. 4A-B, which are schematic illustrations of electrodes 22 and/or 32 disposed on a self-expansible stent 50, in accordance with an embodiment of the present invention. Typically, the stent is inserted into the subject's aorta 24, via a catheter 52. The stent is in a contracted state when it is inside the catheter, and expands automatically inside the aorta upon exiting the distal end 54 of catheter.

Figure 5A:
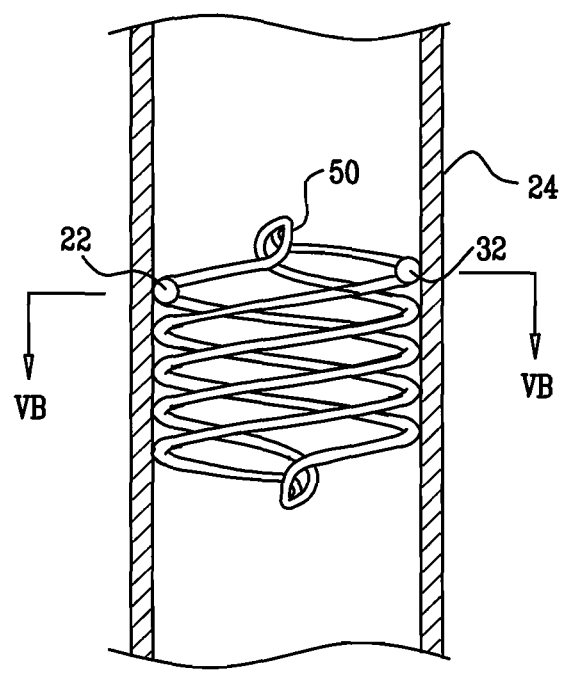
FIGS. 5A-B are schematic illustrations of respective views of a configuration of the self-expansible stent, in accordance with another embodiment of the present invention.
Figure 5B:
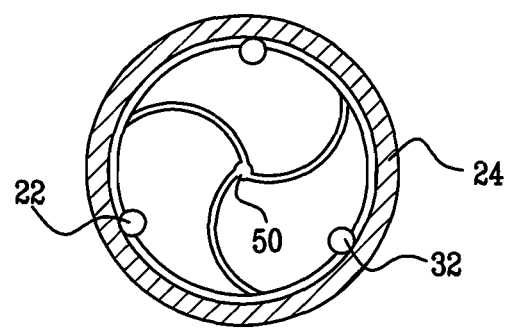

Reference is now made to FIGS. 5A-B, which are schematic illustrations of respective views of a configuration of self-expansible stent 50, in accordance with an embodiment of the present invention. In some embodiments, stent 50 (as shown) is shaped as two or more spirals. The spirals are in contracted states inside catheter 52, and are held in place inside aorta 24 by expanding inside aorta 24.

Figure 6A:
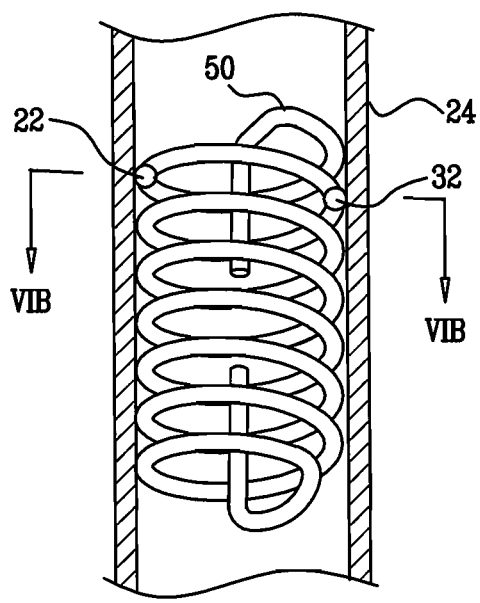
FIGS. 6A-B are schematic illustrations of respective views of an alternative configuration of the self-expansible stent, in accordance with an embodiment of the present invention.
Figure 6B:
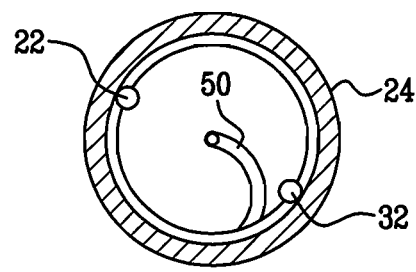

Reference is now made to FIGS. 6A-B, which are schematic illustrations of respective views of an alternative configuration of self-expansible stent 50, in accordance with an embodiment of the present invention. In some embodiments, stent 50 (as shown) is shaped as a coil. The coil is in a contracted state inside catheter 52, and is held in place inside aorta 24 by expanding inside aorta 24.

Figure 7A:
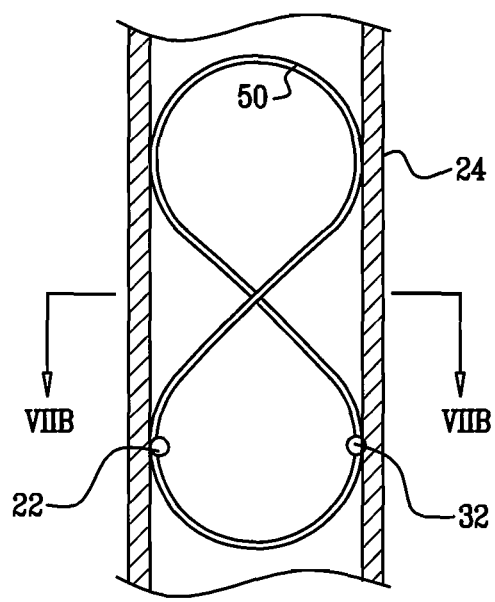
FIGS. 7A-B are schematic illustrations of respective views of a further alternative configuration of the self-expansible stent, in accordance with an embodiment of the present invention.
Figure 7B:
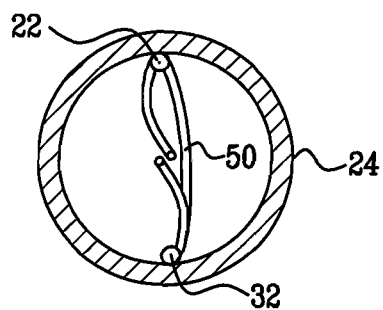

Reference is now made to FIGS. 7A-B, which are schematic illustrations of respective views of a further alternative configuration of self-expansible stent 50, in accordance with an embodiment of the present invention. In some embodiments, stent 50 (as shown) is shaped as a figure-of-eight. The figure-of-eight is in a contracted state inside catheter 52, and is held in place inside aorta 24 by expanding inside aorta 24.

Figure 8:
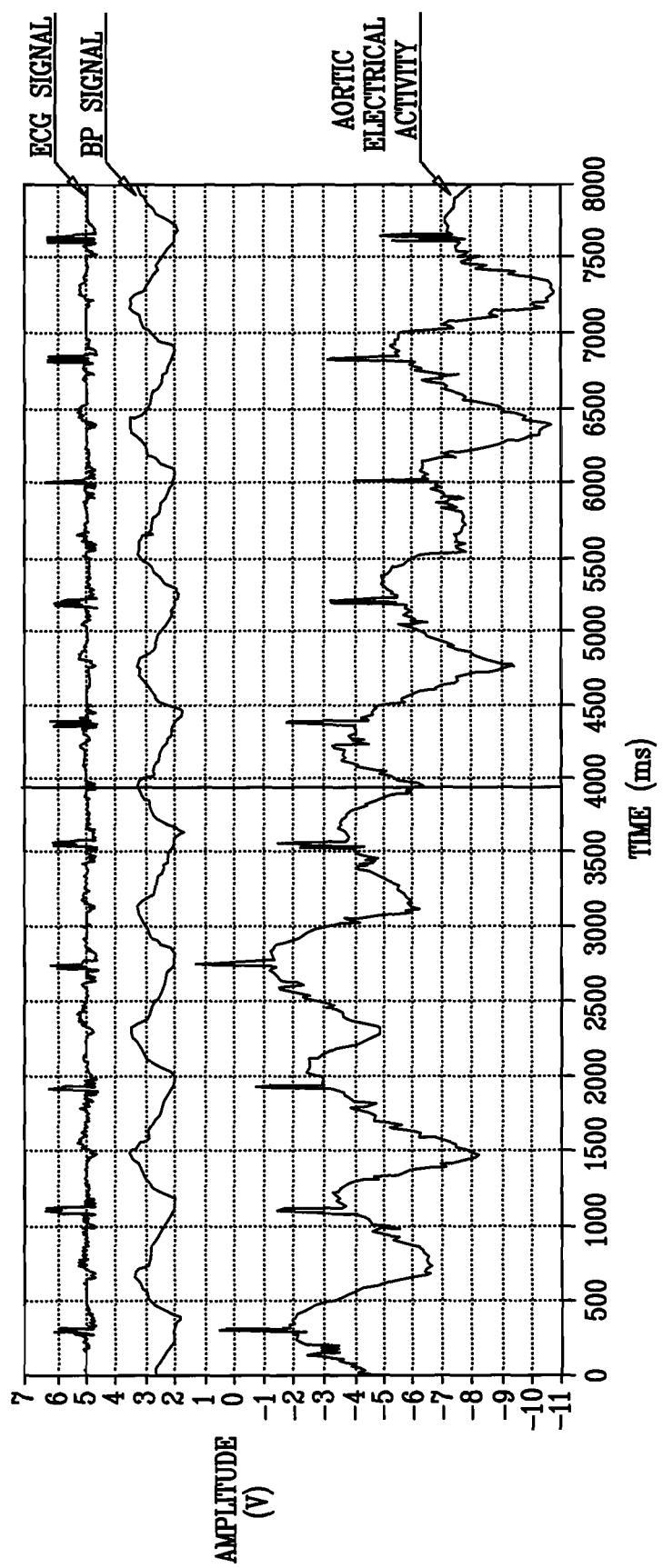
FIG. 8 is a plot of an aortic voltage signal recorded in an aorta of a pig, in an experiment conducted in accordance with an embodiment of the present invention.

Reference is now made to FIG. 8, which is a graph of aortic electrical activity recorded in an aorta of a pig, in an experiment conducted in accordance with an embodiment of the present invention. Ten electrodes were placed in an aorta of a pig close to the aortic valve, and the voltage within the aorta was recorded via four of the ten electrodes. The graph shows the variation of the voltage within the aorta plotted against time. In addition, and concurrently, the pig's ECG and blood pressure were measured. The graph additionally shows the concurrent ECG and blood pressure measurements, which were respectively recorded with an external ECG electrode and with an intra-aortic blood pressure sensor.

Based upon the data in FIG. 8 and in other experiments carried out by the inventors, the inventors have identified relationships between the cardiac cycle and the voltage recorded in the aorta. For example:

(1) There is a sharp peak in the aortic voltage about 50-100 ms before the onset of the aortic pressure rise due to systole. For example, at 2000 ms there is an onset of the pressure rise, and about 70 ms before this onset there is a sharp peak in the aortic voltage.

(2) Shortly before the onset of the aortic pressure decline due to diastole, the aortic voltage reaches a minimum. For example, there is a solid vertical line through the graph at about 3950 ms, at which point, the aortic voltage is at a local minimum. At about 4000 ms, diastole begins.

(3) A signal component in the measured aortic voltage corresponds to, and appears quite similar to, the R-wave recorded with an external ECG electrode, shown in the top trace. For example, the spike in the aortic voltage signal at 6000 ms corresponds to the R-wave in the ECG signal at 6000 ms.

Thus, the inventors have found that important mechanical events (onset of aortic pressure rise and aortic pressure decline) and electrical events (the R-wave) can be identified by aortic sensing, and, in some embodiments, are processed and used to trigger a medical device, such as an intra-aortic balloon pump or a pulse generator.

Figure 9:
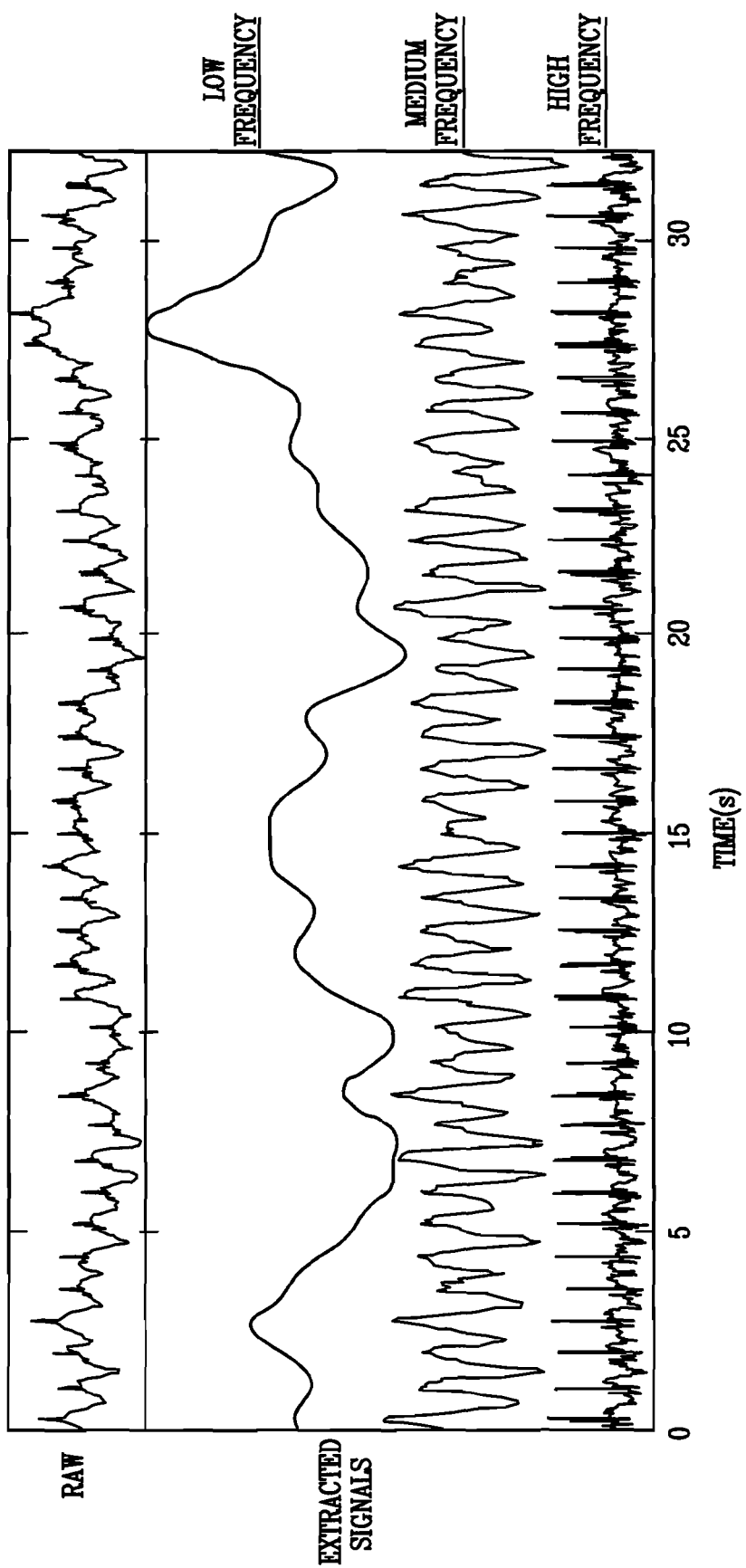
FIG. 9 is a plot showing frequency components of the aortic voltage signal of FIG. 8, as extracted from the raw aortic voltage signal in accordance with an embodiment of the present invention.

Reference is now made to FIG. 9, which is a plot showing frequency components extracted from the raw aortic voltage signal of FIG. 8, in accordance with an embodiment of the present invention. The aortic voltage signal was separated into three frequency components, a low-frequency component, a medium-frequency component, and a high-frequency component.

Figure 10:
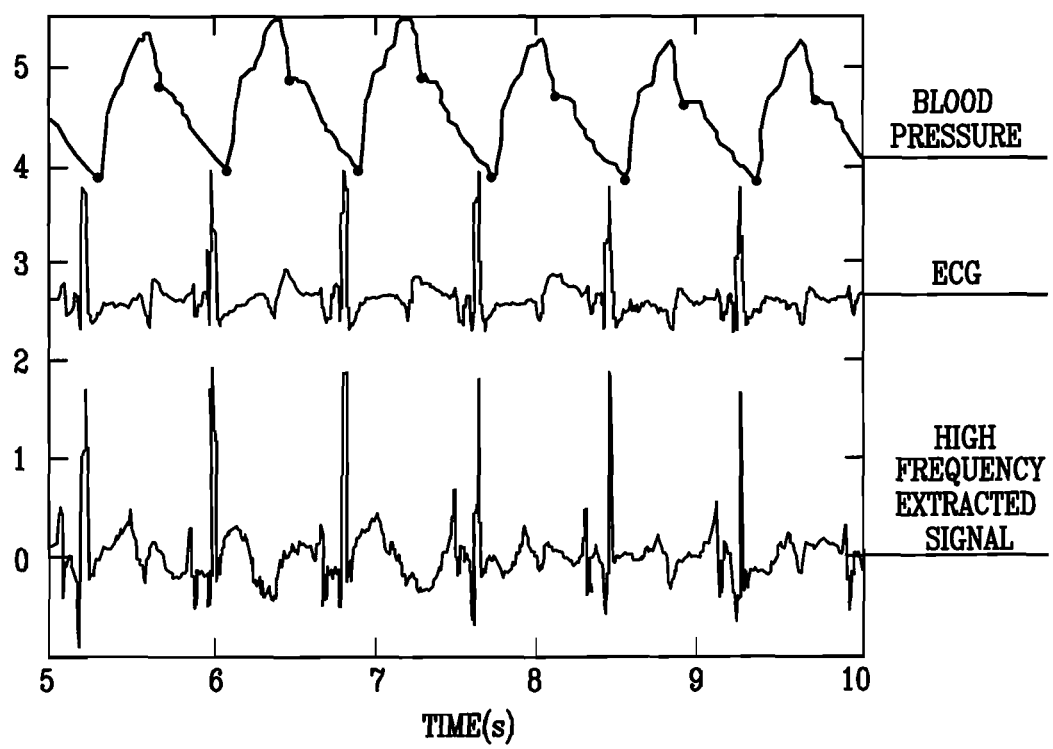
FIG. 10 is a plot comparing a frequency component of the aortic voltage signal of FIG. 8 to the pig's ECG and blood pressure signals, in accordance with an embodiment of the present invention.

Reference is now made to FIG. 10, which shows the high frequency component of the aortic voltage signal plotted together with an ECG recorded by the external electrode and the recorded blood pressure. It was observed by the inventors that the high frequency component has a similar pattern to the ECG signal, as can be seen in FIG. 10. Furthermore, there is a relationship between the occurrence of systole and diastole (which are indicated by the dots on the blood pressure plot), and the plot of the high frequency signal. As such, in embodiments of the invention, an ECG signal of a subject is detected by sensing an electrical parameter in the subject's aorta.

Figure 11:
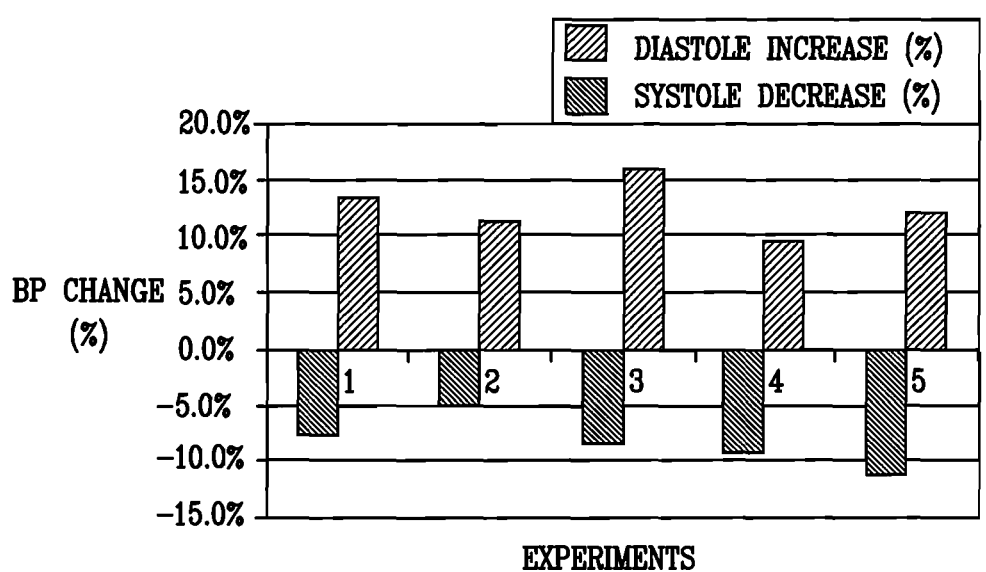
FIG. 11 is a graph showing blood pressure changes measured in five experiments conducted on four pigs, in accordance with an embodiment of the present invention.

Reference is now made to FIG. 11, which is a graph showing blood pressure changes measured in five experiments conducted on four pigs, in accordance with an embodiment of the present invention. In each experiment, the pig was opened surgically, and electrodes (having configurations described hereinbelow) were implanted on the aortic wall. In each of the five experiments, currents having respective parameters were driven into the pigs' aortas during systole and diastole. The systolic currents dilated the aorta (thus decreasing systolic aortic blood pressure), by increasing nitric oxide (NO) secretion by the wall of the aorta. The diastolic currents enhanced constriction of the aorta (thus increasing diastolic aortic blood pressure).

The parameters of the electrodes used, and the currents with which the aortas were stimulated in each of the five experiments, were in accordance with Table 1 below. In Table 1, "Type 1" electrodes denotes Pathfinder electrodes manufactured by Cardima (CA) [product no. 01-161003]. "Type 2" electrodes denotes electrodes, which were custom made for the inventors, each of the custom-made electrodes having a length of 13.3 mm to 13.5 mm, having a diameter of 0.52 mm, and being pointed at a distal end thereof. The custom-made electrodes were oriented to have approximately 10 sq mm of surface area in contact with the wall of the aorta and to be at a minimum distance of 10 mm from each other. All of the electrodes were implanted in the ascending aortas of the pigs.

TABLE 1

| Experiment | Electrode | Systolic current | Diastolic current |
|---|---|---|---|
| 1 | Type 1 | 2 mA monophasic 20 Hz 6 pulses per cardiac cycle | 8 mA monophasic 40 Hz 15 pulses per cardiac cycle |
| 2 | Type 2 | 5 mA monophasic 30 Hz | 12 mA monophasic 80 Hz 15 pulses per |

TABLE 1-continued

| Experiment | Electrode | Systolic current | Diastolic current |
|---|---|---|---|
| 3 | Type 2 | 2 pulses per cardiac cycle 2 mA monophasic 20 Hz 6 pulses per cardiac cycle | cardiac cycle 8 mA monophasic 50 Hz 15 pulses per cardiac cycle |
| 4 (This experiment was performed on the same pig as that of experiment 3) | Type 2 | 2 mA monophasic 12 Hz 4 pulses per cardiac cycle | 7 mA monophasic 50 Hz 16 pulses per cardiac cycle |
| 5 | Type 1 | 1 mA monophasic 20 Hz 6 pulses per cardiac cycle | 10 mA monophasic 60 Hz 4 pulses per cardiac cycle |

The mean decrease in the systolic blood pressure, as a result of the systolic currents, was 8.3±2.3% (mean ±standard deviation). The mean increase in diastolic blood pressure, as a result of the diastolic currents, was 12.4±2.5% (mean ±standard deviation).

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a medical device, comprising:
   a sensing electrode configured to be implanted at a non-cardiac site in a vicinity of an aorta of a subject and to detect an electrical parameter of the aorta; and
   a control unit configured to:
   receive the detected parameter,
   extract first and second signal components from the detected parameter,
   derive an ECG cycle of the subject, from the first component of the detected parameter,
   derive a mechanical event within the aorta, from the second component of the detected parameter, and
   in response to at least one derived parameter selected from the group consisting of: the derived ECG cycle, and the derived mechanical event, control the medical device.

2. The apparatus according to claim 1, wherein the control unit is configured to be disposed in a vicinity of the subject's aorta.

3. The apparatus according to claim 1, wherein the electrode comprises at least a first electrode and a second electrode, the first and second electrodes being configured to be placed within the aorta at a longitudinal distance from each other of between 10 mm and 30 mm.

4. The apparatus according to claim 1, wherein the control unit is configured to drive a current into the aorta in response to the detected parameter.

5. The apparatus according to claim 4, wherein the control unit is configured to detect a cardiac cycle of the subject, based upon the selected derived parameter, and is configured to drive the current in coordination with the subject's cardiac cycle.

6. The apparatus according to claim 5, wherein the control unit is configured to dilate the aorta by increasing nitric oxide (NO) secretion by the wall of the aorta by applying the current.

7. The apparatus according to claim 6, wherein the control unit is configured, based upon the selected derived parameter, to detect systole of the subject, and wherein the control unit is configured to dilate the aorta in response to detecting systole of the subject.

8. The apparatus according to claim 6, wherein the control unit is configured to dilate the aorta by configuring the current to have a frequency of between 5 Hz and 20 Hz.

9. The apparatus according to claim 8, wherein the control unit is configured to dilate the aorta by configuring the current to have a frequency of between 10 Hz and 15 Hz.

10. The apparatus according to claim 6, wherein the control unit is configured to dilate the aorta by configuring the current to have an amplitude of between 1 mA and 5 mA.

11. The apparatus according to claim 10, wherein the control unit is configured to dilate the aorta by configuring the current to have an amplitude of between 2 mA and 3 mA.

12. The apparatus according to claim 5, wherein the control unit is configured, based upon the selected derived parameter, to detect diastole of the subject, and wherein the control unit, in response to detecting diastole of the subject, is configured to enhance constriction of the aorta by driving the current.

13. The apparatus according to claim 5, wherein the control unit,
   is configured, based upon the selected derived parameter, to detect systole and diastole of the subject,
   in response to detecting systole of the subject, is configured to dilate the aorta by increasing nitric oxide (NO) secretion by the wall of the aorta by driving the current, and
   in response to detecting diastole of the subject, is configured to enhance constriction of the aorta by driving the current.

* * * * *